United States Patent [19]

Goldstein et al.

[11] 4,119,407
[45] Oct. 10, 1978

[54] CUVETTE WITH REAGENT RELEASE MEANS

[75] Inventors: Robert H. Goldstein, Tustin, Calif.; Robert M. Stahl, Indianapolis, Ind.

[73] Assignee: Bio-Dynamics, Inc., Indianapolis, Ind.

[21] Appl. No.: 827,123

[22] Filed: Aug. 24, 1977

Related U.S. Application Data

[63] Continuation of Ser. No. 664,623, Mar. 8, 1976, abandoned, which is a continuation of Ser. No. 603,509, Aug. 11, 1975, abandoned.

[51] Int. Cl.² .................... B04B 7/00; G01N 1/10
[52] U.S. Cl. ................................. 422/58; 233/26; 422/72; 422/100; 422/101
[58] Field of Search ............. 23/253 R, 259, 292; 210/DIG. 23; 206/219; 233/26, 1 R

[56] References Cited

U.S. PATENT DOCUMENTS 3,713,775  1/1973  Schmitz ...................... 23/253 R

*Primary Examiner*—Robert M. Reese

*Attorney, Agent, or Firm*—Woodard, Weikart, Emhardt & Naughton

[57] ABSTRACT

A cuvette for holding a liquid specimen during centrifugal testing and analysis of the specimen by a spectrophotometer. The cuvette includes a hollow main body produced from a transparent material to allow analysis of the specimen within the cuvette. Two bags of reagent are mounted within the cuvette main body and are designed to burst upon attainment of a given level of centrifugal force allowing the reagent to flow from the bags into a mixing chamber within the cuvette main body. A plug is sealingly mounted to the lid of the cuvette and is removable to allow insertion of the liquid specimen into the cuvette prior to centrifugal testing. Projections are provided on the cuvette to control the orientation of the cuvette when inserted into a diluter test receptacle. One projection on the cuvette contacts appropriate switch means within the test receptacle in turn operable to activate means for diluting the specimen prior to insertion into the cuvette. A container of desiccant is mounted within the cuvette and is operable to absorb vapors. Means are provided to hold the bags of reagent within the cuvette during centrifugal testing.

14 Claims, 8 Drawing Figures

U.S. Patent  Oct. 10, 1978  Sheet 1 of 4  4,119,407
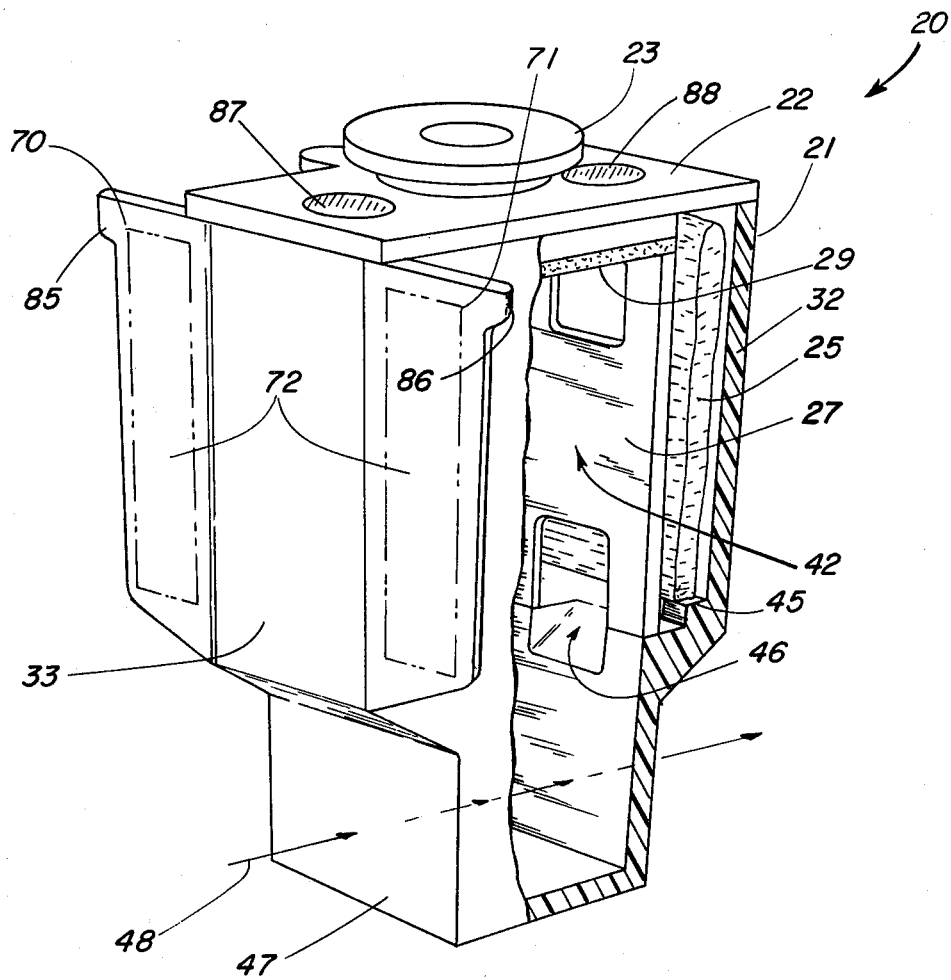
Fig. 1
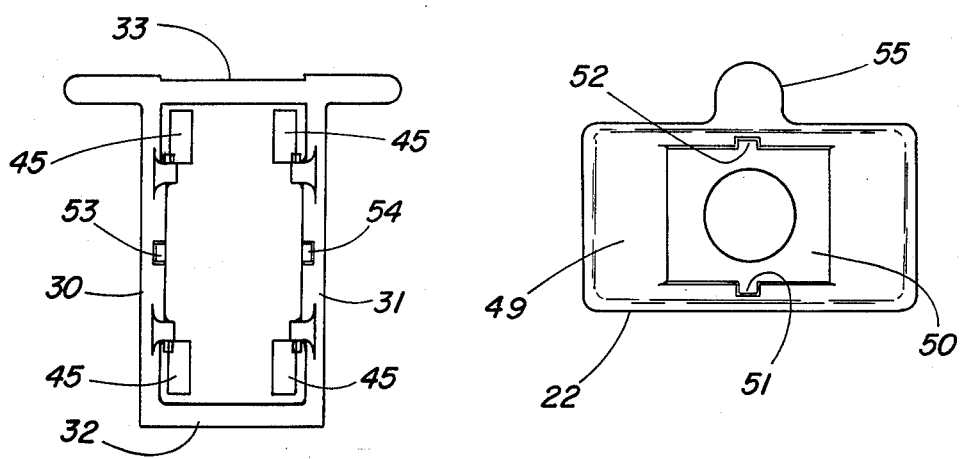
Fig. 3
Fig. 4

CUVETTE WITH REAGENT RELEASE MEANS

This is a continuation of application Ser. No. 664,623, filed Mar. 8, 1976, now abandoned, which is a continuation of Ser. No. 603,509, filed Aug. 11, 1975, now abandoned.

BACKGROUND OF THE INVENTION

1. Field of the Invention

This invention is in the field of containers for holding a specimen undergoing biological testing.

2. Description of the Prior Art

Various prior art devices have been provided for conducting medical tests upon blood specimens. Many of the prior art devices first require that the serum or plasma be separated from the blood prior to the analysis of the serum. In the U.S. Pat. No. 3,713,775 there is disclosed a chemistry analysis system which includes a centrifuge for separating the serum from the blood. After centrifuging, the cuvettes are removed from the centrifuge and placed in a spectrophotometer to determine the amount of light passed through the serum. Alternatively, the amount of light passed can be determined directly while the cuvettes are being spun or turned in the centrifuge.

Disclosed herein is a cuvette for holding specimen during the centrifuging of the specimen and also during analysis of the specimen by a spectrophotometer. The cuvette includes means for holding reagent which is automatically released and mixed with the specimen during centrifuging.

SUMMARY OF THE INVENTION

One embodiment of the present invention is a cuvette for holding a liquid substance during spectrophotometer tests comprising a hollow main body to receive the liquid substance, the main body including at least two opposed end walls to allow testing of the liquid substance by a spectrophotometer while the liquid substance is within the main body, a first bag of reagent positioned within the main body, the bag having bursting means operable to allow the reagent to escape the bag and mix with the liquid substance upon exposing the main body to a predetermined amount of centrifugal force, and a lid sealingly mounted on the hollow main body.

It is an object of the present invention to provide a new and improved cuvette.

A further object of the present invention is to provide a cuvette including means for automatically releasing reagent into specimen contained within the cuvette.

Related objects and advantages of the present invention will be apparent from the following description.

BRIEF DESCRIPTION OF THE DRAWINGS

FIG. 1 is a fragmentary perspective view of a cuvette incorporating the present invention.

FIG. 3 is a top view of the main body of the cuvette taken along the line 3—3 of FIG. 2 and viewed in the direction of the arrows.

FIG. 4 is a bottom view of the cuvette lid shown in FIG. 2.

DESCRIPTION OF THE PREFERRED EMBODIMENT

Figure 2:
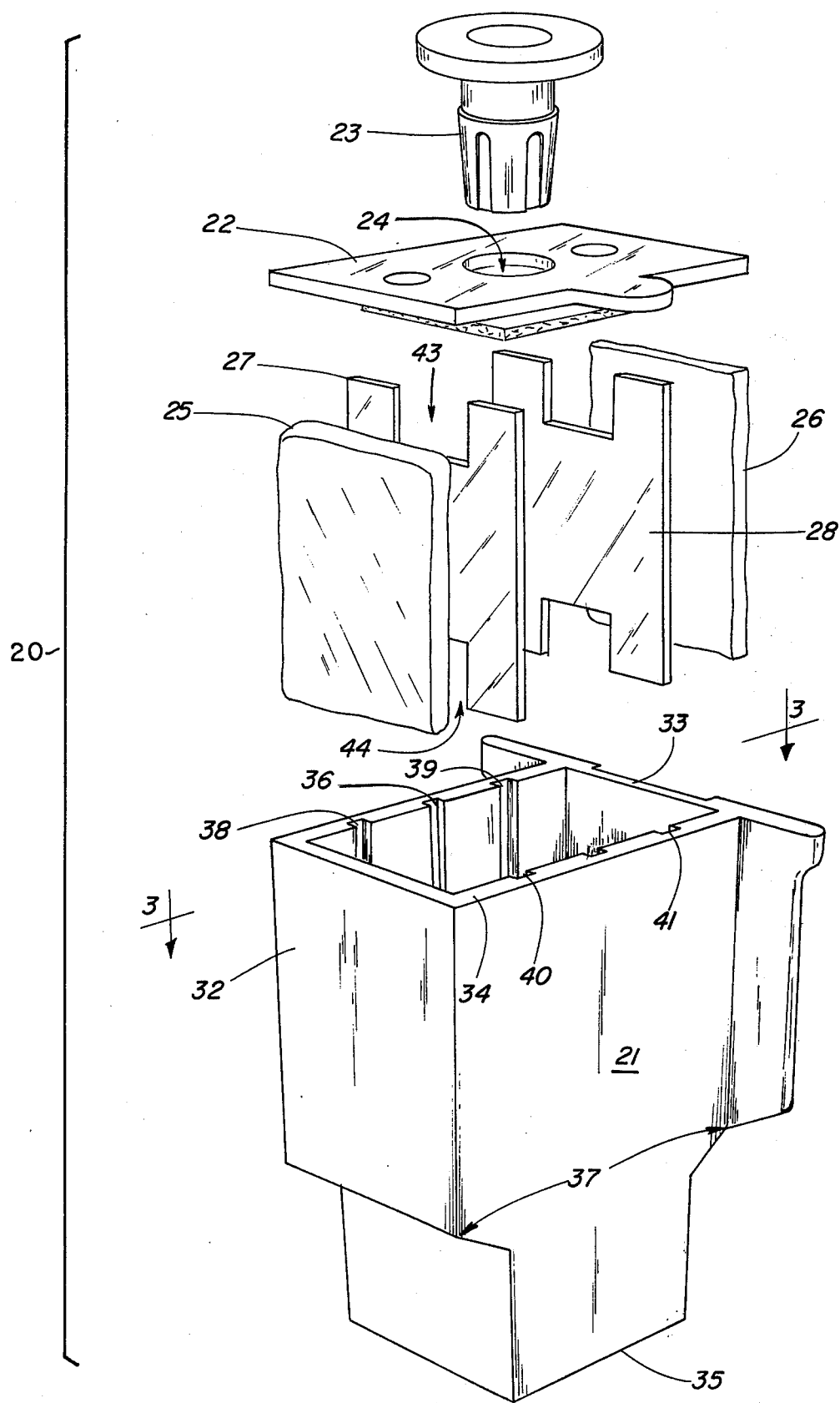
FIG. 2 is a perspective exploded view of the cuvette of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to FIG. 1, there is shown a cuvette 20 for holding a liquid substance during centrifugal fast blood analysis. The cuvette is used to hold the liquid specimen being analyzed by a spectrophotometer. Cuvette 20 includes a hollow main body 21 with a lid 22 sealingly mounted to the main body. A removable plug 23 extends through aperture 24 (FIG. 2) thereby closing and sealing the lid. A pair of reagent bags 25 and 26 are mounted in the cuvette main body 21 and are held in place by a pair of retaining walls 27 and 28. A bag of desiccant 29 is mounted to the bottom surface of lid 22 and absorbs any vapors within the cuvette thereby preventing the vapors from entering the bags of reagents 25 and 26.

Main body 21 includes a pair of side walls 30 and 31 (FIG. 3) integrally joined to a pair of end walls 32 and 33. In one embodiment, the main body was produced from a clear plastic material, such as an Acrylic providing excellent ultraviolet transmission capability. The material was chosen for its ability to pass the entire light spectrum (wave lengths from 340 to 610 nanometers) with at least 80% transmittance. Thus, the specimen while within the cuvette may be analyzed by a spectrophotometer.

Walls 30 and 31 extend parallel from the top edge 34 to the bottom 35 of the main body. Top edge 34 (FIG. 2) extends in a general rectangular configuration forming an opening 36 which is closed by lid 22. A bottom wall is integrally attached at the bottom of the cuvette main body to walls 30 to 33. End walls 32 and 33 (FIG. 2) extend parallel from the top edge 34 of the cuvette main body downwardly to location 37 and then converge inwardly a short distance and then extend downwardly in a parallel relationship to the bottom 35.

Side walls 30 and 31 have mutually facing surfaces with four parallel grooves 38 through 41 (FIG. 2) extending from the top edge 34 downwardly to location 37. Retaining walls 27 and 28 are sized to fit within and be secured by grooves 38 through 41 thereby forming a pair of pockets positioned between end walls 32 and 33 and retaining walls 27 and 28. Reagent bags 25 and 26 fit within the pockets. A mixing chamber 42 (FIG. 1) is thereby formed between the retaining walls and extends downwardly from the lid to the bottom wall of the cuvette.

The reagent bags 25 and 26 are of identical design and thus, the following description as to the bag 25 applies equally to bag 26. Reagent bag 25 is made by scoring a flexible film material with a laser to form a linear depression along approximately the entire length of the film. The film is folded along the linear depression such that there are two sides of approximately equal dimensions and such that the bottom edge of the folded film is the laser scored linear depression. Portions of the two sides of the film are sealed together at predetermined intervals to form a bag having one opened end. The reagent is injected into the bag through the opening which is then sealed. The bags are then inserted into the cuvette and eventually into the centrifuge and violently rupture at a predetermined level of centrifugal force with the reagent then passing from the bag into the mixing chamber of the cuvette thereby mixing with the specimen provided therein. Such a bag is disclosed in the commonly assigned U.S. patent application, Ser. No. 563,562, filed by Robert M. Stahl and entitled BAG which is hereby expressly incorporated by reference.

Each retaining plate is provided with a top and bottom recess to allow the reagent within the adjacent reagent bag to flow into the mixing chamber. For example, retaining wall 27 is provided with recesses 43 and 44 (FIG. 2). Each end wall 32 and 33 is provided with a ledge 45 to seatingly receive a reagent bag. For example, end wall 32 (FIG. 1) is provided with a ledge 45 to seatingly receive the bottom edge of reagent bag 25 thereby positioning the bottom edge of the reagent bag slightly higher than the bottom edge of retaining wall 27. Walls 32 and 33 are provided with recesses which extend from beneath the reagent bags and beneath the retaining walls and into the mixing chamber. For example, end wall 32 is provided with recess 46 (FIG. 1) which directs the reagent into the mixing chamber. Of course, the bottom portions 47 of end walls 32 and 33 (FIG. 1) are completely transparent allowing analysis of the liquid specimen between the end walls by a spectrophotometer as shown by arrow 48.

Walls 27 and 28 are spaced apart respectively from walls 32 and 33 to provide oversized pockets receiving the reagent bags. The reagent bags are not supported by walls 27 and 28 and therefore expand under the force of the centrifuge. The liquid reagent in each bag acts as a column of liquid on the bottom edge of the bag causing the eventual bursting of the bag. Walls 27 and 28 are, however, located sufficiently close to walls 32 and 33 so as to prevent the bags from slipping into the mixing chamber.

The bag of desiccant 29 includes a plastic container fixedly secured to lid 22 by means such as by adhesives. The plastic container holds conventional desiccant to absorb the vapors within the cuvette. The reagent bags as well as the desiccant container are produced from a plastic film. Thus, the plastic used to produce the reagent container has a higher permeability as compared to the plastic body of the reagent bags thereby insuring that the vapors are absorbed by the desiccant container and not the reagent bags.

The bag of reagent may be produced from Aclar film which has a low permeability. The total amount of vapor evaporated through the film into the cuvette from the bag of reagent may be 40 microliters per year. This vapor could continue to shorten the shelf lyophilized enzyme material enclosed in the cuvette. In order to prevent the vapor from being absorbed by the lyophilized enzyme material, a vapor absorbing chemical is packaged in the desiccant container which is produced from plastic having a high permeability.

Lid 22 (FIG. 4) has a bottom surface 49 with a generally rectangular projection 50 provided thereon which extends into the cuvette main body. A pair of tabs 51 and 52 are provided and are complimentarily received by a pair of notches 53 and 54 of side walls 30 and 31 (FIG. 3) to prevent relative motion between the lid and the cuvette main body. The lid may be sealed to the cuvette main body by means such as ultrasonic welding.

Figure 5:
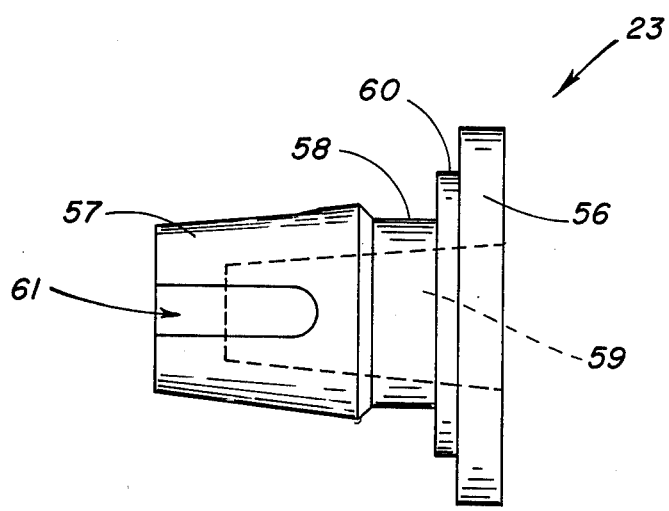
FIG. 5 is an enlarged side view of the plug shown in FIG. 2.

Plug 23 is produced from a semi-flexible material, such as rubber. Integrally attached to the top wall 56 of the plug is a tapered and cylindrical bottom portion 57 being attached to the top wall by a necked down portion 58 (FIG. 5). A hole 59 extends through the top wall and into the tapered portion of the plug allowing the tapered portion to compress as the plug is forced into the aperture of the lid. Of course, hole 59 does not extend completely through the plug and thus, the plug seals the cuvette when inserted through the lid. The largest diameter of the tapered portion 57 is greater than the diameter of the lid aperture and will therefore compress as the plug is inserted into the lid. When plug 23 is completely inserted into the lid aperture, the lid is positioned adjacent to the necked down portion 58. A cylindrical washer 60 is integrally formed on the bottom surface of top wall 56 of the plug to thereby space top wall 56 slightly above the top surface of lid 22. It is therefore possible to insert a tool beneath the top wall of the plug and to subsequently pry the plug from the lid. Tapered portion 57 is beveled immediately adjacent necked down portion 58 to prevent the plug from accidental disengagement from the cuvette. A plurality of grooves 61 are provided in the outer surface of the tapered end of the plug to facilitate the compression of the tapered end as the plug is inserted into the cuvette. In certain cases, a bag of reagent will not be inserted into the cuvette and instead, the reagent will be placed into the cuvette being free to move throughout the main body of the cuvette. In the event the reagent is to be freeze-dried, then plug 23 is partially inserted into the cuvette allowing moisture to be withdrawn through the lid via grooves 61 until eventually the plug is fully inserted. Thus, grooves 61 allow moisture to escape the cuvette during the lyophilization process.

Figure 6:
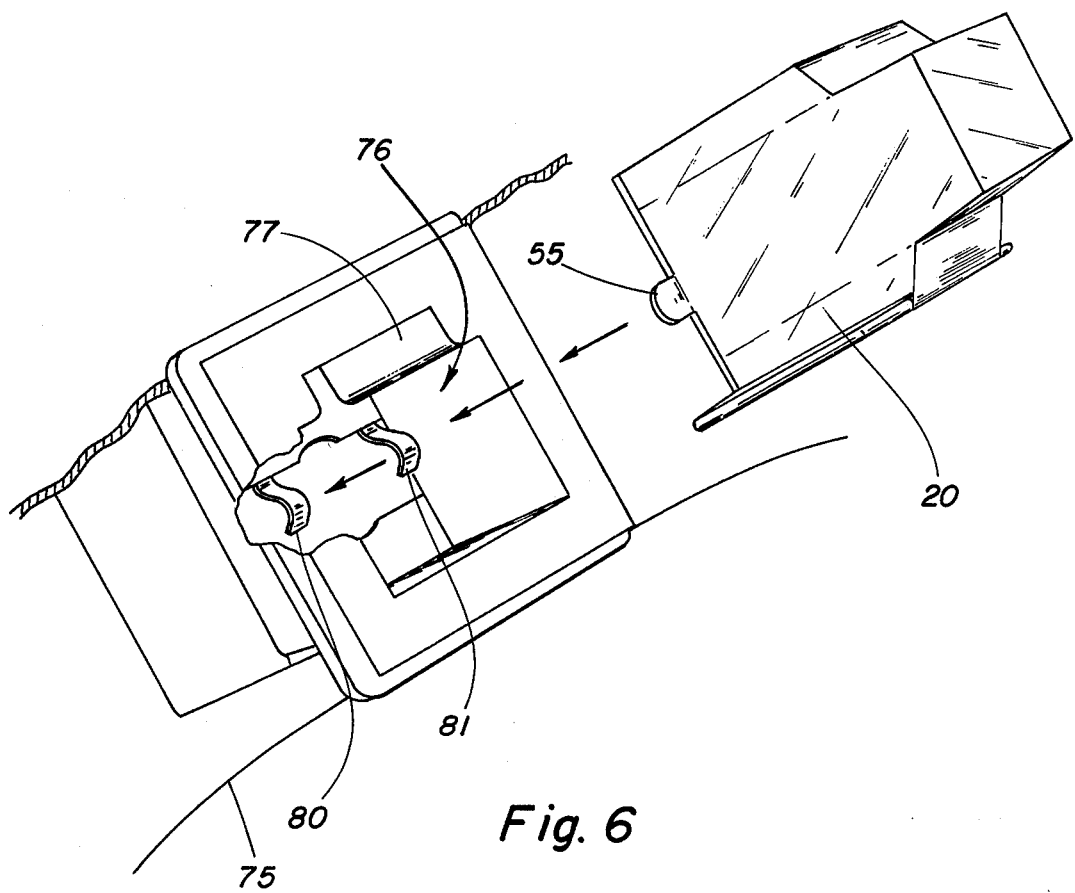
FIG. 6 is a fragmentary perspective view of the cuvette of FIG. 1 being inserted into a cuvette receptacle.

A pair of flanges 70 and 71 are integrally attached to end wall 33 (FIG. 1). Flanges 70 and 71 project outwardly of side walls 30 and 31 and are provided to receive various markings in areas 72 with the markings indicating the test name, a test number and various codes. Additional information may be marked on areas 87 and 88 on lid 22 (FIG. 1). The flanges extend outwardly of the main body of the cuvette to allow optical reading of the test codes and insertion of the cuvette into a test receptacle in only one given direction. Shown in FIG. 6 is an apparatus 75 including a test receptacle 76 for receiving cuvette 20. End 77 of test receptacle 76 is of a smaller dimension and thus can receive the cuvette only if end wall 32 is inserted into the receptacle adjacent end 77 as contrasted to end wall 33 which is larger including flanges 70 and 71. Thus, the cuvette may be inserted into the test receptacle only when the cuvette is oriented in a given direction with respect to the receptacle.

Various tests may be conducted on the specimen within the cuvette. Certain tests require the specimen to be diluted by a greater amount as compared to other tests. Likewise, varying amounts of specimen are used depending upon the particular test. The cuvettes are premarked in areas 72 to indicate the proper cuvette to be used with the particular test. Once plug 23 is removed, the diluted specimen may be inserted into the cuvette and the plug reinserted through the lid. To insure that the correct dilution of the specimen is provided as required by the particular test, a tab 55 extends outwardly from lid 22 and outwardly of the cuvette main body. Except for tab 55, the lid is symmetrical and thus, the lid may be originally installed either positioning tab 55 adjacent side wall 30 or adjacent side wall 31. In those tests requiring the specimen to be diluted only a small amount, tab 55 is positioned adjacent, for example, side wall 30 whereas tab 55 is positioned, for example, adjacent side wall 31 when the particular test requires a large dilution of the specimen. Apparatus 75 automatically provides the correct amount of specimen dilution depending upon the orientation of tab 55.

A pair of microswitches 80 and 81 are positioned at the bottom of test receptacle 76 and are contacted and activated by tab 55 depending upon the orientation of tab 55. For example, by inserting the cuvette into the test receptacle as shown in FIG. 6, tab 55 will contact switch 80 thereby activating the diluter operated by switch 80. The cuvette is then withdrawn and the appropriate amount of diluted specimen is then inserted through the lid by the diluter. Likewise, tab 55 may be positioned on the opposite side of the cuvette as compared to FIG. 6 with the result that switch 81 will be activated by the tab providing for the correct amount of dilution once the cuvette is withdrawn from the test receptacle and connected to the diluter.

Figure 7:
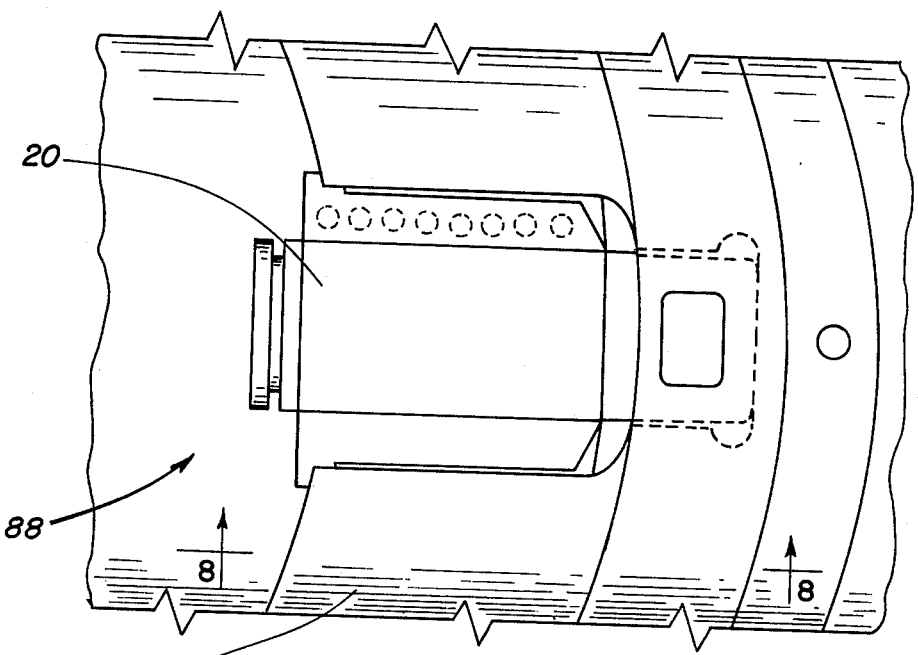
FIG. 7 is a fragmentary top view of a centrifuge with the cuvette of FIG. 1 installed therein.
Figure 8:
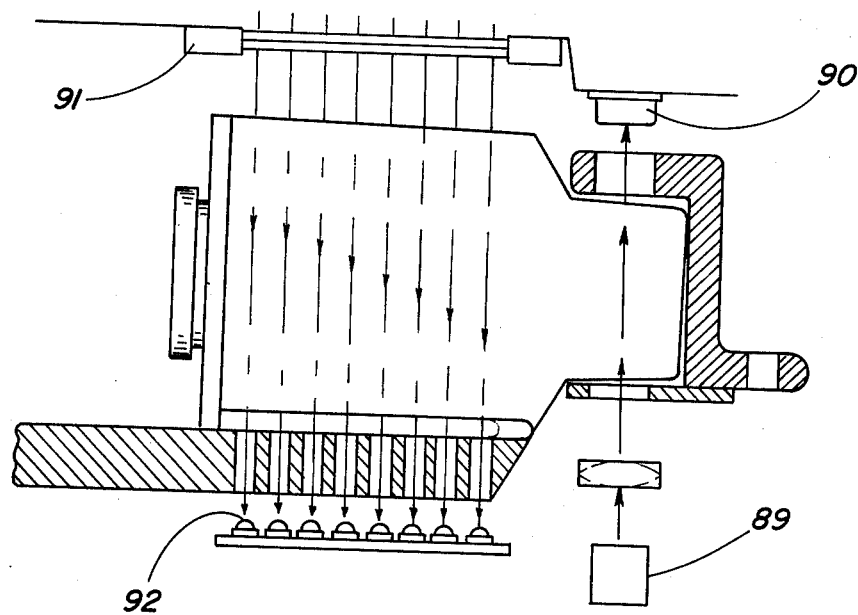
FIG. 8 is a cross-sectional view taken along the line 8—8 of FIG. 7 and viewed in the direction of the arrows.

A portion of a typical centrifuge 85 is shown in FIGS. 7 and 8 and includes a recess 88 for receiving cuvette 20. A spectrophotometer is provided which has a source of energy 89 which passes through the bottom portion of the cuvette being sensed by sensor 90. Likewise, a source of energy 91 is provided for sending beams of energy through flanges 70 and 71 with the matters marked thereon being sensed by sensor 92. Thus, the cuvette may be inserted into the centrifuge which includes automatic controls for activating the spectrophotometer. Wall 33 of the cuvette includes a pair of ears 85 and 86 (FIG. 1) allowing the cuvette to be held in place when positioned in the centrifuge.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is: said main

1. A cuvette for holding a liquid substance during spectrophotometer tests comprising:
    a hollow main body to receive said liquid substance, said main body including at least two opposed end walls to allow testing of said liquid substance by a spectrophotometer while said liquid substance is within said main body;
    a first bag of reagent positioned within said main body, said bag having bursting means operable to allow said reagent to escape said bag and mix with said liquid substance upon exposing said main body to a predetermined amount of centrifugal force, said bag of reagent including an outer main body of plastic sheet of a predetermined permeability;
    desiccant means mounted in said hollow main body being operable to absorb vapor within said hollow main body prior to said vapor being absorbed by said bag of reagent, said desiccant means including a container of desiccant attached to said lid, said container including an outer wall of plastic of a permeability higher than said predetermined permeability of said bag of reagent; and
    a lid sealingly mounted on said hollow main body.

2. A cuvette for holding a liquid substance during spectrophotometer tests comprising:
    a hollow main body to receive said liquid substance, said main body including at least two opposed end walls to allow testing of said liquid substance by a spectrophotometer while said liquid substance is within said main body;
    a first bag of reagent positioned within said main body, said bag having bursting means operable to allow said reagent to escape said bag and mix with said liquid substance upon exposing said main body to a predetermined amount of centrifugal force; and
    a lid sealingly mounted on said hollow main body, said lid including a tab extending outwardly of said main body, said lid being mounted to said main body to position said tab in a different orientation relative to said main body depending on the dilution and quantity of said liquid substance to be inserted into said main body.

3. The cuvette of claim 2 wherein:
    said main body includes a flange extending outwardly therefrom with a stop surface on said flange allowing the insertion of said cuvette into a given test receptacle only when said main body is in a given orientation relative to said receptacle.

4. The cuvette of claim 3 wherein:
    said lid includes an aperture extending therethrough; and further comprising:
    a removable plug mounted to said lid and sealing said aperture.

5. The cuvette of claim 3 and further comprising:
    surface means provided on said flange operable to cooperate with separate means apart from said cuvette to indicate the test to be performed with said cuvette.

6. A container for holding a diluted specimen during centrifugal and spectrophotometer testing comprising:
    a main body to hold said diluted specimen and possessing sufficient strength to not deteriorate during centrifugal testing, said main body including transparent portions to allow said diluted specimen to be analyzed by a spectrophotometer while said specimen is located within said main body; said main body including a pair of side walls, said side walls including mutually facing surfaces and a groove formed on each of said surfaces;
    a retaining wall slidably received in said grooves forming a pocket within said main body and,
    a first container of reagent within said pocket in said main body, said container having release means operable to release reagent from said first container and from said pocket and into said main body during centrifugal testing.

7. The cuvette of claim 6 wherein:
    said bag of reagent includes a film which has a first side and a second side, said first side and said second side are joined by sealing at three seams, said first side and said second side have a single non-sealed common edge, said bag further includes a scored linear depression in said common edge such that said common edge is of predetermined strength sufficiently weak to burst and open under the action of force creating means to permit the flow of a reagent out of the bag.

8. The cuvette of claim 6 and further comprising:
desiccant means mounted in said hollow main body being operable to absorb vapor within said hollow main body prior to said vapor being absorbed by said bag of reagent.

9. The cuvette of claim 6 wherein:
said lid includes an aperture extending therethrough; and further comprising:
a removable plug mounted to said lid and sealing said aperture.

10. The container of claim 6 wherein:
said main body includes a pair of end walls and a pair of side walls, said side walls include mutually facing surfaces and parallel grooves formed on said surfaces; and further comprising:
a pair of spaced apart retaining walls slidably received in said grooves forming a pair of pockets between said end walls and said retaining walls, said retaining walls are parallel forming a mixing chamber extending therebetween;
a second container of reagent located in one of said pockets with said first container of reagent located in the other of said pockets.

11. The container of claim 10 wherein:
said end walls extend parallel along the length of said retaining walls and then converge beneath said pockets to direct reagent from said first bag and said second bag into said mixing chamber when said first bag and said second bag open.

12. The container of claim 11 wherein:
at least a portion of said end walls are parallel beneath said retaining walls, said portion of each end wall is transparent to allow analysis by a spectrophotometer of said specimen within said cuvette.

13. A cuvette for holding a liquid substance during spectrophotometer tests comprising:
a hollow main body to receive said liquid substance, said main body including at least two opposed end walls to allow testing of said liquid substance by a spectrophotometer while said liquid substance is within said main body;
a lid sealingly mounted on said hollow main body, said lid including a tab extending outwardly of said main body, said lid being mounted to said main body to position said tab in a different orientation relative to said main body depending on the dilution and quantity of said liquid substance to be inserted into said main body;
said main body including a flange extending outwardly therefrom with a stop surface on said flange allowing the insertion of said cuvette into a given test receptacle only when said main body is in a given orientation relative to said receptacle; and
reagent within said main body.

14. The cuvette of claim 13 wherein:
said lid includes an aperture extending therethrough; and further comprising:
a removable plug mounted to said lid and sealing said aperture.

* * * * *